United States Patent [19]

Sugiyama et al.

[11] 4,435,587

[45] Mar. 6, 1984

[54] PROCESS FOR PRODUCING SILICON ISOCYANATE COMPOUNDS

[75] Inventors: Iwakichi Sugiyama, Narashino; Kiyoshi Endo, Inba; Yukihisa Takaoka, Inashiki, all of Japan

[73] Assignee: Matsumoto Seiyaku Kogyo Kabushiki Kaisha, Japan

[21] Appl. No.: 406,961

[22] Filed: Aug. 10, 1982

[30] Foreign Application Priority Data

Aug. 19, 1981 [JP] Japan .................................. 56-128734

[51] Int. Cl.³ ................................................ C07F 7/10
[52] U.S. Cl. ...................................... 556/410; 556/411
[58] Field of Search ................................ 556/410, 411

[56] References Cited

U.S. PATENT DOCUMENTS 3,093,451 6/1963 Weisse et al. ................... 556/411 X
3,113,146 12/1963 Fielding et al. ...................... 556/411
3,642,854 2/1972 Kozjukov et al. .............. 556/411 X

FOREIGN PATENT DOCUMENTS 66232 5/1982 European Pat. Off. ............ 556/410

Primary Examiner—Paul F. Shaver
Attorney, Agent, or Firm—Wenderoth, Lind & Ponack

[57] ABSTRACT

A process for producing a silicon isocyanate compound which comprises reacting a silicon halide compound in which a fluoride compound is excluded with an isocyanate of the formula [I] $M(NCO)_m$ or a cyanate of the formula [I'] $M(OCN)_m$ wherein M represents a member selected from the group consisting of alkali metals and alkaline earth metals, and m is 1 or 2, in the presence of one or more reaction accelerators selected from the group consisting of alkylene glycols, polyalkylene glycols and, ether and ester derivatives thereof, thereby to prepare a silicon isocyanate compound containing at least one Si—NCO linkage.

10 Claims, No Drawings

PROCESS FOR PRODUCING SILICON ISOCYANATE COMPOUNDS

BACKGROUND OF THE INVENTION

The present invention relates to a novel process for producing silicon isocyanate compounds. More specifically, the present invention relates to a novel process for producing silicon isocyanate compounds which comprises reacting a silicon halide compound with an alkali salt of isocyanic acid or cyanic acid in the presence of a reaction accelerator.

A silicon isocyanate compound readily reacts with a compound containing a hydroxyl group or amino group to form a silyl urea linkage or siloxane linkage. Therefore, the silicon isocyanate compound is useful as an intermediate or a raw material for various organosilicon compounds or a material for various compositions.

The term "silicon isocyanate compound" as used herein refers to a compound containing one or more Si—NCO linkages. Such a compound has been hitherto prepared by reacting a silicon compound containing a Si—X linkage, wherein X represents a halogen atom, with silver isocyanate or lead cyanate. However, such a conventional process provides a poor yield and is disadvantageous from an economical point of view because an expensive silver or lead salt is used as a starting material of the reaction. For this reason, it would be advantageous if salts of alkali metals such as sodium and potassium, and alkaline earth metals such as barium or ammonium, which are relatively easily available, could be used in place of the silver or lead salt. These metallic salts, however, are not satisfactory with respect to reactivity. Therefore, these metallic salts have been considered to be unsuitable for use in the production of a silicon isocyanate compound.

DOS No. 1,965,741 (published July 8, 1971) discloses that a silicon isocyanate compound can be synthesized by reacting an alkali metal cyanate or ammonium isocyanate with a silicon halide in the presence of a certain reaction accelerator. As the reaction accelerator, a specially selected compound having a dielectric constant of 10 or more, such as acid amides and N-methylpyrrolidone is used. Also, the process disclosed in the above-mentioned patent publication uses an organic solvent having a relatively high boiling point such as cyclohexanone and benzonitrile. The use of such a solvent is inconvenient in view of the reaction operation. Therefore, the process is not advantageous for practical purposes.

In view of the above described state of the art, we have made studies to obtain a silicon isocyanate compound containing Si—NCO linkage(s) from the reaction of an alkali metal, alkaline earth metal or ammonium salt of cyanic acid or isocyanic acid, which salt is easily available, with a silicon halide compound in a higher yield at a lower cost as compared with the conventional process. As a result, we have discovered that the use of a reaction accelerator selected from alkyl amines, nitroalkanes and crown ethers can produce a silicon isocyanate compound in a high yield while the amount of the reaction accelerator added is reduced to a low level. Thus, the present inventors have applied for a patent (Japanese Patent Application No. 101647/1979).

In accordance with the above mentioned process, a silicon isocyanate compound can be produced from a silicon halide compound and an isocyanate or cyanate salt, which is inexpensive and has low toxicity. Therefore, the process is considered to be advantageous as compared with the conventional process. However, there is room for further improvement in the process, because alkyl amines, nitroalkanes and crown ethers, which are used as the reaction accelerator, require special handling, and the product is difficult to separate and refine from the reaction mixture.

SUMMARY OF THE INVENTION

An object of the present invention is to provide a process for producing advantageously a silicon isocyanate compound which comprises reacting a silicon halide compound with an isocyanate or cyanate in the presence of a reaction accelerator which has a high reaction accelerating action, is simple and safe to handle, and affords easy separation of the product from the reaction mixture.

Our investigations and experiments have revealed that alkylene glycols, polyalkylene glycols or ethers or esters thereof (including halogen-substituted derivatives thereof) are useful as such a reaction accelerator.

Accordingly, the present invention provides a novel process for producing a silicon isocyanate compound containing Si—NCO linkage(s) which comprises reacting a silicon halide compound, particularly, a member selected from the group consisting of compounds having the formula [II] $R_nSiX_{4-n}$ or [III] $(RO)_nSiX_{4-n}$ wherein R represents a saturated or unsaturated organic radical; X represents a halogen atom except fluorine; and n is 0 or an integer of from 1 to 3, partially condensed products thereof and silicon halides having the silicon skeleton

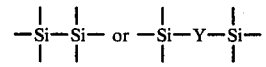

in which Y represents a hydrocarbon radical, with an isocyanate of the formula [I] $M(NCO)_m$ or a cyanate of the formula [I'] $M(OCN)_m$ in which M represents a member selected from the group consisting of alkali metals and alkaline earth metals; and m is 1 or 2, if necessary, in a solvent which is substantially unreactive to both the above mentioned materials and the reaction product, in the presence of one or more reaction accelerators selected from the group consisting of alkylene glycols, polyalkylene glycols, and ether and ester derivatives thereof (including halogen derivatives thereof).

The nature, utility, and further features of this invention will be more clearly apparent from the following detailed description beginning with a consideration of general aspects of the invention and concluding with specific examples of practice thereof. Throughout the following description, quantities expressed in percent and parts are by weight.

DETAILED DESCRIPTION OF THE INVENTION

The silicon halide compounds usable for the present invention are those of the formulae [II] and [III] in which R represents a saturated or unsaturated organic radical such as methyl, ethyl, propyl, butyl, octyl, decyl, stearyl, behenyl, vinyl, phenyl, naphthyl, benzyl, allyl, propargyl, ethoxymethyl, ethoxyethyl, ethoxypropyl, butoxydiethyleneglycoxyethyl, pentafluoroethyl, and heptafluoropropyl, and X represents a halogen, except fluorine, particularly chlorine or bromine.

The partially condensed products of the above mentioned silicon halide compounds include hexachlorodisiloxane, dimethyltetrachlorodisiloxane, and tetramethyldichlorodisiloxane.

Examples of the compounds having the silicon skeleton

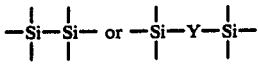

are 1,2-dimethyltetrachlodisilane, hexachlorodisilane, bis(chlorodimethylsilyl)methane, 1,2-bis(chlorodimethylsilyl)ethane, bis(trichlorosilyl)methane and p-bis(chlorodimethylsilyl)benzene.

In the above mentioned formula [I] and [I'], M represents a member selected from the group consisting of alkali metals such as lithium, sodium and potassium, alkaline earth metals such as magnesium, calcium and barium and ammonium. Of the compounds of the formulae [I] and [I'], sodium cyanate is particularly suitable from a practical point of view. In this connection, it is noted that cyanic acid (H—O—C≡N) and isocyanic acid (H—N=C=O) are mutually tautomers. It is known that the silver or ammonium salt is present in the form of an isocyanate and the alkali metal or lead salt is present in the form of a cyanate. Also, it is considered that the corresponding silicon compound is usually in the form of isocyanate, namely

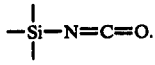

The reaction accelerator constituting a feature of the present invention can be selected from the group consisting of alkylene glycols, e.g. ethylene glycol, propylene glycol, butylene glycol and octylene glycol, and halogen-substituted derivatives thereof; polyalkylene glycols, e.g. polyethylene glycol, polypropylene glycol and polybutylene glycol, and halogene-substituted derivatives thereof; mono- and di-ether derivatives of alkylene glycols and polyalkylene glycols in which the ether-forming moiety is a member selected from the group consisting of hydrocarbon radicals such as methyl, ethyl, propyl, butyl, oleyl, stearyl, benzyl and phenyl and furfuryl; mono- and di-ether derivatives of polyhydroxy compounds such as glycerol, sorbitol and sucrose; and mono-, di- and tri-ester derivatives of alkylene glycols and polyalkylene glycols in which the ester-forming moiety is a member selected from carboxylic acids such as acetic acid, butyric acid, octanoic acid, lauric acid, stearic acid, fumaric acid, maleic acid, adipic acid, benzoic acid, lactic acid, glycolic acid, levulinic acid, phthalic acid, trimellitic acid, benzophenondicarboxylic acid, citric acid, tartaric acid and gluconic acid.

These reaction accelerators may be used singly or in combination depending on the desired reactivity. Particularly, ethylene glycol, polyethylene glycol and derivatives thereof are highly reactive and easy to use. Of these reaction accelerators, those compounds which are of the structure exhibiting a HLB value of at least 10.5, preferably at least 13.5, calculated according to the standard of HLB calculation method for a surface active agent are especially favored.

The reaction is conveniently carried out in an organic solvent. That is, a solution of a silicon halide compound dissolved in an organic solvent is dropped into an organic solvent suspension of a mixture of a salt of cyanic acid or isocyanic acid with a small amount of a reaction accelerator while the mixture is stirred. Thereafter, the resultant mixture is heated under reflux to carry out the reaction. After the resultant precipitate is filtered off, the remaining filtrate is subjected to removal of the organic solvent thereby to obtain the intended product. In accordance with this process, the silicon halide compound can be converted into the corresponding isocyanate compound in a significantly high yield. The product can be refined by distillation or recrystallization.

More specifically, in accordance with the present invention, the reaction can be carried out without using any solvent. However, it is desirable that the reaction be carried out in the presence of a solvent selected from organic compounds incapable of changing the properties of both the starting materials and the reaction product. Examples of the solvent usable for the reaction are hydrocarbons and halogenated hydrocarbons, such as n-hexane, cyclohexane, petroleum ether, benzene, toluene, chloroform, trichloroethylene, 1,1,2,2-tetrachloroethane and chlorobenzene. It is preferable that these solvents be used in a quantity sufficient to disperse completely an isocyanate or cyanate therein. Ordinarily, the isocyanate or cyanate is used in a stoichiometrical or excessive quantity with respect to the quantity of the halogen which is contained in the silicon halide compound and is to be substituted therewith. If the amount of the isocyanate or cyanate is less than the stoichiometrical quantity, the resultant product will inevitably be accompanied by the unreacted material. An excessive amount is also disadvantageous from an economical point of view. Ordinarily, 1.1 to 3 times the stoichiometrical amount of the isocyanate or cyanate may be used taking into consideration of reaction rate and the like. The reaction is preferably carried out while the reaction mixture is stirred so as to sufficiently disperse the isocyanate or cyanate therein.

The reaction may be carried out at a temperature lower than room temperature. However, in this case, a long period of time of 5 hours or more is necessary to complete the reaction. A reaction temperature higher than 200° C. remarkably accelerates the reaction, but may cause undesired side reactions. Therefore, the reaction is advantageously carried out at a temperature of from room temperature to 150° C., preferably, from 40° to 100° C. The reaction can be substantially completed at the above mentioned temperature within a period of time of from 20 minutes to 2 hours.

When the quantity of the reaction accelerator is less than 0.01% based on the weight of the silicon halide compound, it sometimes takes 5 hours or more to complete the reaction. Also, in the case where the quantity of the reaction accelerator is more than 20% based on the weight of the silicon halide compound, the reaction may be accelerated, but the silicon compound reacts with a hydroxyl group if the reaction accelerator contains the group therein. This additional reaction results in a reduction in yield of the intended product. Therefore, the reaction accelerator is used in a quantity ranging ordinarily from 0.05 to 10%, preferably, from 0.2 to 4.0% with respect to the quantity of the silicon halide compound.

Thus, in accordance with the present invention, by using as the reaction accelerator, alkylene glycols, polyalkylene glycols or, ethers or esters thereof (including halogen-substituted derivatives thereof), a silicon isocyanate compound can be obtained in a high yield from a silicon halide compound and a cyanate such as sodium cyanate or an isocyanate which is easily available. Therefore, the process of the present invention is advantageous as compared with the conventional process using silver isocyanate or lead cyanate as the starting material. Further, a very small amount of the reaction accelerator used in the process of the present invention is sufficient. Accordingly, the process of the present invention is advantageous from the viewpoint of the production cost and the reaction operation as compared with the process disclosed in DOS No. 1,965,741.

The silicon isocyanate compound containing Si—NCO linkage(s) obtained by the process of the present invention easily reacts with a compound containing, in the molecule, active hydrogen, such as an alcohol, a primary amine, a secondary amine or a carboxylic acid. Therefore, the silicon isocyanate compound of the present invention can be used as a modifier or a component for polymers to impart the properties of silicon to the polymers.

In order to indicate more fully the nature and utility of this invention, the following specific examples of practice thereof are set forth, it being understood that these examples are presented as illustrative only and are not intended to limit the scope of the invention.

EXAMPLE 1

77 parts of dimethyldichlorosilane were dissolved in 60 parts of toluene. 86 parts of dehydrated sodium cyanate and 1 part of ethylene glycol were added to the solution thus obtained. The resultant mixture was heated with stirring at a temperature of 60° C. for 1 hour to carry out a reaction.

The reaction mixture was cooled to a temperature of 20° C., which step was followed by filtration. From the filtrate toluene was removed, and the residue was distilled to obtain 79 parts of a colorless liquid having a boiling point of from 138° to 140° C. at a pressure of 760 mmHg. The yield of the intended product was 92% calculated in terms of chlorosilane.

The liquid product contained no chlorine and exhibited a strong absorption of $\nu$NCO at a wavenumber of 2270 cm$^{-1}$ when subjected to infrared absorption analysis. Elemental analysis of the product indicated: Si, 19.45%; C, 33.16%; H, 4.15%; and N, 18.69%, which closely corresponded to the values of Si, 19.72%; C, 33.81%; H, 4.22% and N, 19.71% calculated for dimethyl silicon diisocyanate.

EXAMPLE 2

17.3 parts of silicon tetrachloride, 33.1 parts of dehydrated sodium isocyanate and 1 part of polyethylene glycol (7 EG) nonylphenyl ether were added to 50 parts of benzene. The resultant mixture was caused to react by heating with stirring at a temperature of 50° C. for 1.5 hours.

The reaction mixture was cooled to a temperature of 20° C. and thereafter filtered. From the filtrate benzene was removed, and the residue was distilled to obtain 15 parts of a colorless liquid having a boiling point of from 105° to 106° C. at a pressure of 35 mmHg (yield 73%).

The liquid product contained no chlorine and exhibited an absorption of $\nu$NCO at a wavenumber of 2270 cm$^{-1}$ when subjected to infrared absorption analysis. Furthermore, the product exhibited a Si content of 14.21% which closely corresponded to a Si value of 14.28% calculated for silicon isocyanate Si(NCO)$_4$.

EXAMPLES 3 THROUGH 23

Various isocyanate compounds as indicated in the following table were synthesized in a manner similar to that described in Example 1.

Boiling point determination and infrared analysis indicated that all of these products were the intended silicon isocyanates.

In the Examples, "butyl cellosolve" is a trade name of monobutyl ether of ethylene glycol and "Tween 20" is an ethylene oxide condensate of sorbitan monolaurate.

| Example | Raw material R$_n$SiX$_{4-n}$ | part | M(NCO)$_m$ or M(OCN)$_m$ M of the above formulae | part | Reaction accelerator | part | Yield part (%) | Boiling point °C./mmHg | Si content % |
|---|---|---|---|---|---|---|---|---|---|
| 3 | (CH$_3$)$_3$SiCl | 11 | Sodium | 9.7 | Diethylene glycol monomethyl ether | 0.8 | 8.9 (80) | 91/760 | 23.86 |
| 4 | (CH$_3$)$_2$SiCl$_2$ | 13 | Sodium | 19.5 | Dipropylene glycol monomethyl ether | 1.5 | 10.7 (76) | 139/760 | 19.32 |
| 5 |  SiCl$_3$ | 29.5 | Sodium | 29.1 | Tetraethyleneglycol | 1.0 | 20.1 (85) | 250/760 | 11.63 |
| 6 | 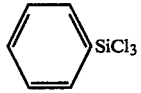 SiCl$_3$ | 29.5 | Magnesium | 29.8 | Polyethylene glycol (7EG)monobutyl ether | 1.0 | 19.9 (84) | 250/760 | 11.70 |
| 7 | CH$_2$=CHSiCl$_3$ | 16.2 | Sodium | 29.1 | Tetraethylene glycol monoacetate | 1.0 | 15.0 (83) | 125/50 | 15.33 |
| 8 | (C$_4$H$_9$)$_3$SiCl | 23.5 | Sodium | 9.7 | Butylcellosolve | 1.0 | 18.3 (76) | 160/50 | 11.37 |
| 9 | (CH$_3$)$_3$SiCl | 11 | Potassium | 12.1 | Diethylene glycol monochloromethyl ether | 1.0 | 8.8 (80) | 90/760 | 24.21 |
| 10 | (CH$_3$)$_3$SiCl | 11 | Sodium | 9.7 | Propylene glycol | 1.0 | 6.9 | 90/760 | 24.01 |

-continued

| Example | Raw material $R_nSiX_{4-n}$ | part | M(NCO)$_m$ or M(OCN)$_m$ M of the above formulae | part | Reaction accelerator | part | Yield part (%) | Boiling point °C./mmHg | Si content % |
|---|---|---|---|---|---|---|---|---|---|
|  |  |  |  |  |  |  | (60) |  |  |
| 11 | 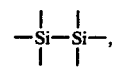SiCl$_3$ | 29.5 | Potassium | 36.3 | Polyethylene glycol 2000 | 1.0 | 14.9 (63) | 250/760 | 11.71 |
| 12 | (CH$_3$)$_3$SiCl | 11 | Sodium | 9.7 | Butylene glycol | 1.0 | 6.6 (57) | 91/760 | 24.14 |
| 13 | (CH$_3$)$_3$SiCl | 11 | Sodium | 9.7 | C$_9$H$_{17}$(OCH$_2$CH$_2$)$_2$OCH$_3$ | 1.0 | 8.6 (75) | 91/760 | 23.89 |
| 14 | (CH$_3$)$_3$SiCl | 11 | Sodium | 9.7 | Tween 20 | 1.0 | 7.8 (68) | 90/760 | 23.99 |
| 15 | (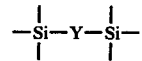)$_3$SiCl | 30 | Sodium | 9.7 | Tetraethylene glycol dimethyl ether | 1.0 | 22.5 (75) | 198/50 | 9.21 |
| 16 | CH$_3$OSiCl$_3$ | 8.2 | Sodium | 10.7 | Polyethylene glycol 20000 | 0.2 | 5.2 (58) | 154/760 | 15.14 |
| 17 | C$_4$H$_9$OSiCl$_2$<br>\|<br>CH$_3$ | 18.7 | Sodium | 14.3 | Polyethylene glycol 2000 | 0.3 | 12.0 (60) | 125/50 | 14.02 |
| 18 | CH$_3$(OCH$_2$CH$_2$)$_2$OSiCl$_3$ | 25.3 | Sodium | 21.5 | Polyethylene glycol 20000 | 0.6 | 10.9 (40) | 140/5 | 10.31 |
| 19 | (CH$_3$O)$_2$SiCl$_2$ | 7.1 | Sodium | 14.3 | Diethylene glycol monomethyl ether | 0.2 | 13.0 (75) | 152/760 | 16.09 |
| 20 | ⌬OSiCl$_3$ | 22.7 | Sodium | 21.5 | Butylene glycol monoacetate | 0.5 | 14.6 (59) | 252/760 | 17.01 |
| 21 | [Cl(CH$_3$)$_2$Si]$_2$O | 20.3 | Sodium | 14.3 | Triethylene glycol dimethyl ether | 0.5 | 17.3 (80) | 91/30 | 12.94 |
| 22 | (CH$_3$)$_3$SiSi(CH$_3$)$_2$Cl | 17.0 | Potassium | 9.5 | Tween 20 | 1 | 6.9 (40) | 160/760 | 8.05 |
| 23 | (CH$_3$CH$_2$O)$_3$SiCl | 20.0 | Potassium | 9.5 | Triethylene glycol monoethyl ether | 0.5 | 12.3 (60) | 173/760 | 6.81 |

We claim:

1. A process for producing a silicon isocyanate compound which comprises reacting a silicon halide compound selected from the group consisting of silicon chloride compounds, silicon bromide compounds and silicon iodide compounds with an isocyanate of the formula [I] M(NCO)$_m$ or a cyanate of the formula [I'] M(OCN)$_m$ wherein M represents a member selected from the group consisting of alkali metals and alkaline earth metals, and m is 1 or 2, in the presence of one or more reaction accelerators selected from the group consisting of alkylene glycols, polyalkylene glycols, ether and ester derivatives thereof and halogen-substituted derivatives thereof, thereby to prepare a silicon isocyanate containing at least one Si—NCO linkage.

2. A process as claimed in claim 1, wherein said silicon halide compound is a member selected from the group consisting of (i) compounds having the formula R$_n$SiX$_{4-n}$, (ii) compounds having the formula (RO)$_n$SiX$_{4-n}$, (iii) compounds having the silicon skeleton $$-\underset{|}{\overset{|}{Si}}-\underset{|}{\overset{|}{Si}}-,$$

(iv) compounds having the skeleton $$-\underset{|}{\overset{|}{Si}}-Y-\underset{|}{\overset{|}{Si}}-$$

and (v) partially condensed products of the above-mentioned compounds (i) through (iv), wherein R represents a saturated or unsaturated organic radical; n is 0 or an integer of from 1 to 3; X is chlorine, bromine or iodine atom; and Y represents a hydrocarbon radical.

3. A process as claimed in claim 1, wherein the reaction is carried out in the presence of a solvent substantially unreactive with respect to both the starting materials and the reaction product.

4. A process as claimed in claim 3, wherein said solvent is a member selected from the group consisting of hydrocarbons and halogenated hydrocarbons.

5. A process as claimed in claim 1, wherein the reaction is carried out at a temperature of from room temperature to 150° C.

6. A process as claimed in claim 5, wherein the reaction is carried out at a temperature of from 40° to 100° C.

7. A process as claimed in claim 1, wherein the isocyanate or cyanate is used in a stoichiometrical or excessive molar quantity per mole of the halogen contained in the silicon halide compound.

8. A process as claimed in claim 7, wherein the isocyanate or cyanate is used in a quantity of from 1.1 to 3 times the stoichiometrical quantity of the isocyanate or cyanate with respect to the halogen contained in the silicon halide compound.

9. A process as claimed in claim 1, wherein the reaction accelerator is used in a quantity of from 0.05 to 10% by weight based on the weight of the silicon halide compound.

10. A process as claimed in claim 9, wherein the reaction accelerator is used in a quantity of from 0.2 to 4.0% by weight based on the weight of the silicon halide compound.

* * * * *